US012688942B2

(12) United States Patent
Zhang et al.

(10) Patent No.: US 12,688,942 B2
(45) Date of Patent: Jul. 21, 2026

(54) DUAL-MODE MOBILE Wi-Fi OTOSCOPE SYSTEM AND METHODS

(71) Applicants: Jane Yuqian Zhang, Bothell, WA (US); Zhan Wang, Newcastle, WA (US)

(72) Inventors: Jane Yuqian Zhang, Bothell, WA (US); Zhan Wang, Newcastle, WA (US)

(73) Assignee: REMMIE, INC., Wilmington, DE (US)

( * ) Notice: Subject to any disclaimer, the term of this patent is extended or adjusted under 35 U.S.C. 154(b) by 41 days.

(21) Appl. No.: 18/702,446

(22) PCT Filed: Oct. 27, 2022

(86) PCT No.: PCT/US2022/047992

§ 371 (c)(1),
(2) Date: Apr. 18, 2024

(87) PCT Pub. No.: WO2023/076454

PCT Pub. Date: May 4, 2023

(65) Prior Publication Data

US 2024/0412879 A1     Dec. 12, 2024

Related U.S. Application Data

(60) Provisional application No. 63/272,637, filed on Oct. 27, 2021.

(51) Int. Cl.
*G16H 80/00* (2018.01)
*A61B 1/00* (2006.01)
(Continued)

(52) U.S. Cl.
CPC ......... *G16H 80/00* (2018.01); *A61B 1/00016* (2013.01); *A61B 1/00045* (2013.01);
(Continued)

(58) Field of Classification Search
None
See application file for complete search history.

(56) References Cited

U.S. PATENT DOCUMENTS

2013/0211265 A1     8/2013     Bedingham et al.
2014/0073880 A1     3/2014     Boucher et al.
(Continued)

FOREIGN PATENT DOCUMENTS

WO     WO-2023076454 A1     5/2023

OTHER PUBLICATIONS

Ansary et a. ("The virtual physical exam in the 21st century." Journal of telemedicine and telecare 27.6 (2021): 382-392) (Year: 2021).*

(Continued)

*Primary Examiner* — Christopher B Tokarczyk
(74) *Attorney, Agent, or Firm* — Arch & Lake LLP

(57)     ABSTRACT

An improvement in the telemedicine-based diagnosis of acute otitis media is discussed. The improvement including a system and method for merging an otoscope video stream into a telemedicine session. Operations for merging the otoscope video stream can being with initiating a telemedicine session. Subsequently, the system can determine, from within the telemedicine session, whether a connection to an otoscope providing the otoscope video stream is available. If the video stream is available, the system can access the otoscope video stream within the telemedicine session.

19 Claims, 4 Drawing Sheets

(51) Int. Cl.
　　　*A61B 1/227*　　　(2006.01)
　　　*G16H 40/63*　　　(2018.01)
　　　*G16H 40/67*　　　(2018.01)

(52) U.S. Cl.
　　　CPC ............. *A61B 1/227* (2013.01); *G16H 40/63*
　　　　　　　　　(2018.01); *G16H 40/67* (2018.01)

(56)　　　　　　　References Cited

U.S. PATENT DOCUMENTS

| | | |
|---|---|---|
| 2015/0261930 A1 | 9/2015 | Espinosa Escalona et al. |
| 2018/0110475 A1* | 4/2018 | Shaya .................... G16H 10/60 |
| 2018/0192965 A1* | 7/2018 | Rose .................... A61B 5/0002 |
| 2020/0037930 A1 | 2/2020 | Abramoff et al. |
| 2020/0152324 A1 | 5/2020 | Stein et al. |
| 2021/0068646 A1 | 3/2021 | Zhang et al. |
| 2022/0054008 A1* | 2/2022 | Venkatraman ......... G16H 50/70 |

OTHER PUBLICATIONS

"International Application Serial No. PCT/US2022/047992, International Search Report mailed Feb. 9, 2023", 2 pgs.
"International Application Serial No. PCT/US2022/047992, Written Opinion mailed Feb. 9, 2023", 4 pgs.
"OMRON connect US/CAN App iOS Pairing Video", OMRON Healthcare US, [Online] Retrieved from the internet: <https://www.youtube.com/watch?v=jYodua72IXA>, (Feb. 8, 2021), 3 pgs.

* cited by examiner

DUAL-MODE MOBILE Wi-Fi OTOSCOPE SYSTEM AND METHODS

PRIORITY APPLICATIONS

This application is a U.S. National Stage Filing under 35 U.S.C. 371 from International Patent Application Serial No. PCT/US2022/047992, filed Oct. 27, 2022, which application claims the benefit of priority to U.S. Patent Application Ser. No. 62/272,637, filed Oct. 27, 2021, the contents of which are hereby incorporated by reference in their entirety entireties.

BACKGROUND

Acute Otitis Media (AOM, or ear infection) is the most common reason for a sick child visit in the US as well as low to mid income countries. Ear infections account for the most common reason for antibiotics usage for children under 6 years, particularly in the 24-month to 3 age group. It is also the second most important cause of hearing loss, impacting 1.4 billion in 2017 and ranked fifth highest disease burden globally.

During a physician's visit, the standard practice for diagnosing an AOM requires inserting an otoscope with a disposable speculum in the external ear along the ear canal to visualize the tympanic membrane (eardrum). A healthy eardrum appears clear and pinkish-gray, whereas an infected one will appear red and swollen due to fluid buildup behind the membrane. Access to otolaryngology, pediatric, or primary specialist is severely limited in low resource settings, leaving AOM undiagnosed or misdiagnosed. The primary unmet needs with an ear infection are the lack of means to track disease progression, which could lead to delayed diagnosis at onset or ineffective treatment.

During a physician's visit, an otoscope with a disposable speculum is inserted in the external ear along the ear canal to visualize the tympanic membrane (eardrum). A healthy eardrum appears clear and pinkish-gray, whereas an infected one will appear red and swollen due to fluid buildup behind the membrane. However, these features are not immediately distinguishable especially when there is limited time to view the eardrum especially of a squirmy child using a traditional otoscope.

Telemedicine provides a viable means for in-home visits to a provider with no wait time and closed-loop treatment guidance or prescription. An ear infection is an ideal candidate for real-time telemedicine visits, but due to the lack of means to visualize inside the ear, telemedicine provider cannot accurately diagnose an ear infection. As a result, telemedicine was found to lead to over-prescription of antibiotics or "new utilization" of clinical resources which would otherwise not occur compared to in-person visits.

Overview

The present inventors identified an opportunity to improve the telemedicine experience and remote diagnosis of AOM or related issues through use of a telemedicine application and connected otoscope to provide real-time imaging of a patient's ear to a remote physician. One of the challenges identified by the current inventors was the difficulty of introducing a real-time video stream from a camera equipped otoscope into an on-going telemedicine session. One avenue to enable a telemedicine session between a patient and a remote physician involves establishing an Internet Protocol (IP) based audio and/or video session (commonly referred to as a video conference) via a proprietary application or a commonly available IP conferencing tool, such as Zoom or WebEx™. However, once a video conference is established introducing a secondary video source into the conference presented a difficulty and was not supported by standard tools such as Zoom or WebEx™.

Accordingly, the current inventors developed a solution including a mobile application for iPhone® or Android® and a mobile Wi-Fi enabled otoscope with an integrated camera to stream a video image of a patient's ear, nose, or throat. The otoscope includes all of the features and functions discussed in a related application, application Ser. No. 17/044,285, titled "PORTABLE OTOSCOPE", which is hereby incorporated by reference in its entirety. The solution developed provides two different modes of operation for connection to the Wi-Fi enabled otoscope, the first mode of operation is called station mode and involves the Wi-Fi otoscope connecting to a common Wi-Fi network (e.g., a local network) to communicate with the mobile device running the telemedicine application. The second mode involves the Wi-Fi otoscope broadcasting its own Wi-Fi network for direct connection to the mobile device and is intended for use in situations where no local network is available. The second mode of operation is called AP mode (Access Point mode).

As noted above, the invention involves a dual-mode mobile Wi-fi otoscope that connects to Apple/iOS or Android mobile devices and the Internet via either 1) access point mode, in which the otoscope emits a local Wi-fi network as a hot spot for the mobile device; or 2) station mode, in which the otoscope and the mobile device both connect to the same ambient Wi-fi network. The camera lens is the smallest on the market with 3.7 mm diameter, compared to existing solutions which are 3.9 mm, 4.5 mm or above, making it usable on both children and adults (previous solutions are too large for children). The dual-mode connection solves the problem that a user would not be able to connect to the Internet and to stream symptoms in a remote telemedicine platform, while concurrently displaying images and videos on both iOS and Android mobile devices locally.

Currently available Wi-fi personal care camera or ear wax removing cameras only connect with a mobile device with access point mode, i.e., while connecting to these devices to visualize symptoms, the mobile device loses external Internet connection via Wi-fi as its Wi-fi port is occupied. These typical personal care cameras cannot connect to telehealth (telemedicine) applications to allow users to share symptoms with a remote care telehealth provider concurrently. To get online to access the internet while these products are connected to the mobile devices, Apple phone can leverage data/LTE connections to access the Internet, while Android phones does not allow dual Wi-Fi/LTE connections, therefore not possible to connect to the Internet. None of the devices leverage station mode transmission to share, transmit, or store data in secure cloud.

The invention can be delivered as part of a platform that interfaces with a software development kit (SDK) or App to seamlessly integrate device, information, and analytics into telehealth platforms. The otoscope can be used at-home and in point-of-care for collecting, transmitting, streaming, and sharing ear, nose, throat, skin, oral including teeth symptoms directly with a healthcare provider via virtual visits.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

A system and method for early and remote diagnosis of ear disease is disclosed. An images of a patient's inner ear may be taken with an otoscope and transmitted to a cloud-based database and/or shared in real-time with a physician via a telemedicine application or platform.

An otitis media is most commonly diagnosed using an otoscope (FIG. 1), essentially a light source with a magnifying eyepiece for visualization of the ear canal and eardrum with the human eye. Typical otoscopes lack communication functions requisite for the current invention but can be incorporated after the communication functions are fulfilled by complementing devices. The dual-mode mobile Wi-Fi enabled otoscope described herein can provide real-time imaging of a patient's ear, nose, or throat to a telemedicine application or platform via a mobile device or via cloud-base service.

In one embodiment, an otoscope is disclosed that is configured to be used together with a host device, such as a smart phone or other handheld mobile devices. The handheld mobile device, such as an iPhone® from Apple, Inc., can receive a live video stream from the otoscope 100 over a Wi-Fi connection either directly between the mobile device 110 and the otoscope (AP mode) or via a local network (station mode).

The otoscope includes a camera module driven by a system-on-a-chip (SoC) chipset that supports a range of resolution data rates. In an example, the SoC chipset supports 720p resolution data rates with H.264 encoding. The otoscope includes a Linux operating system and firmware supporting the encoding/decoding of video stream. In an example, the camera module has the smallest diameter 3.7 mm, which can be used on both children and adults. In an example, the SoC chipset and firmware can drive both the camera module, Wi-Fi module, and video/image streaming/processing. In an example, firmware operating on the otoscope utilizes telecommunication protocols that encrypt for both access point and station mode connections, allowing on-chip data processing, transmission, streaming via local Wi-Fi to a mobile device close by, or transmission through local router network to access the Internet, and secure data storage cloud. In these examples, compatible chipset-firmware-camera-software App operates as a complete SoC/IoT system to ensure data capture, transmission, sharing, and storage both on local mobile device, via the Internet, and secure data storage cloud. The data is stored both on local mobile device, as well as secure cloud data base. If when the data is saved the phone is connected to the otoscope AP, i.e., no Internet access, data will be uploaded to cloud after the Internet connection is recovered.

Figure 1:
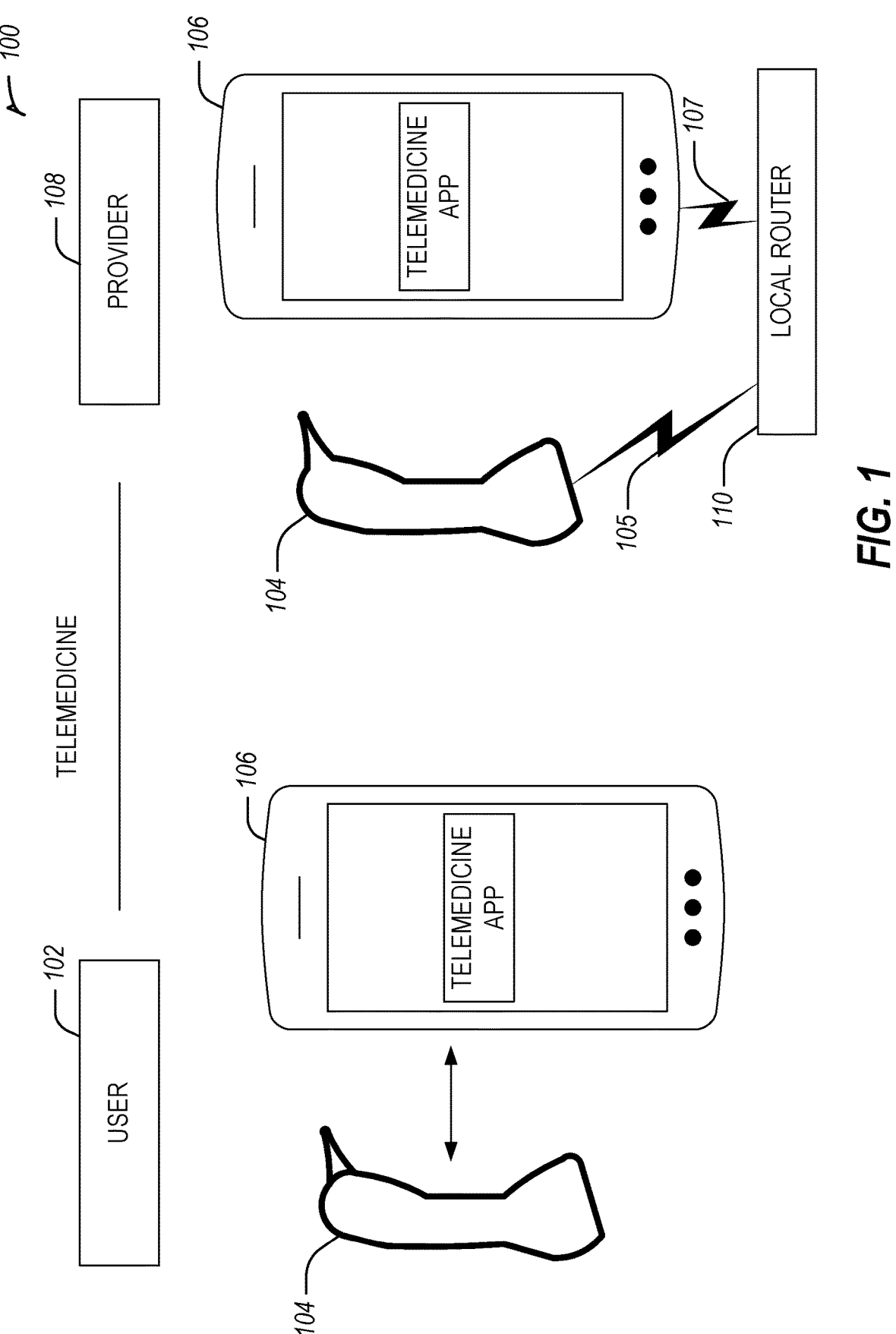
FIG. 1 illustrates a platform for ear nose and throat disease state diagnostic support in accordance with at least one example of this disclosure.

FIG. 1 illustrates a platform 100 for ear nose and throat disease state diagnostic support using a telemedicine application and a video enabled otoscope in accordance with at least one example of this disclosure. The platform 100 includes a user ecosystem 102 and a provider ecosystem 108. The two ecosystems 102 and 108 may perform various functions, with some overlap and some unique to the ecosystem. In some examples, the user ecosystem 102 and the provider ecosystem 108 are remote from each other (e.g., a patient may be at home using the user ecosystem 102, while a doctor operates the provider ecosystem 108 from an office), and in other examples the ecosystems 102 and 108 may be local to each other, such as when a patient visits a doctor's office. The devices of the user ecosystem 102 and the provider ecosystem 108 may communicate (e.g., via a network, wirelessly, etc.) with each other and with devices within each ecosystem.

In an example, the user ecosystem 102 includes an otoscope 104 and a user device 106 (e.g., a mobile device such as a phone or a tablet, a computer such as a laptop or a desktop, a wearable, or the like). The otoscope 104 may be communicatively coupled to the user device 106 (e.g., configured to send data such as an image over a wired or wireless connection, such as Bluetooth, Wi-Fi, Wi-Fi direct, near field communication (NFC), or the like). In some examples, functionality of the otoscope 104 may be controlled by the user device 106. For example, the user device 106 may trigger a capture of an image or video at the otoscope 104. The triggering may be caused by a user selection on a user interface on the user device 106, caused automatically (e.g., via a detection of an object within a camera view of the otoscope 104, such as an ear drum), or via remote action (e.g., by a device of the provider ecosystem 108). When the trigger is via a remote action, the remote action may include a provider selection on a user interface of a device of the provider ecosystem 108 indicating that the camera view of the otoscope 104 is acceptable (e.g., a capture will include an image of an ear drum or other anatomical feature of a patient).

The otoscope 104 may be used to capture an image or video stream of an ear drum or inner ear portion of a patient. When the image/video is captured, it may be sent to the user device 106, which may in turn send the image a device of the provider ecosystem 108 via a telemedicine application running on the device 106 and in communication with a cloud-base server hosting the telemedicine session. In an example, the mobile device 106 establishes a direct connection to the otoscope 104 over a Wi-Fi network broadcast from the otoscope. In another example, the mobile device 106 and the otoscope 104 communicate over a local network (e.g., via local router 110). In this example, the mobile device 106 is connected to the local network via connection 107 and the otoscope 104 is connected to the same local network via connection 105. In some examples, the otoscope 104 can re-establish connection 105 at power up and be available for connection to a telemedicine session operating within an application (App) running on a mobile device, such as mobile device 106, connected to the same network.

Figure 2:
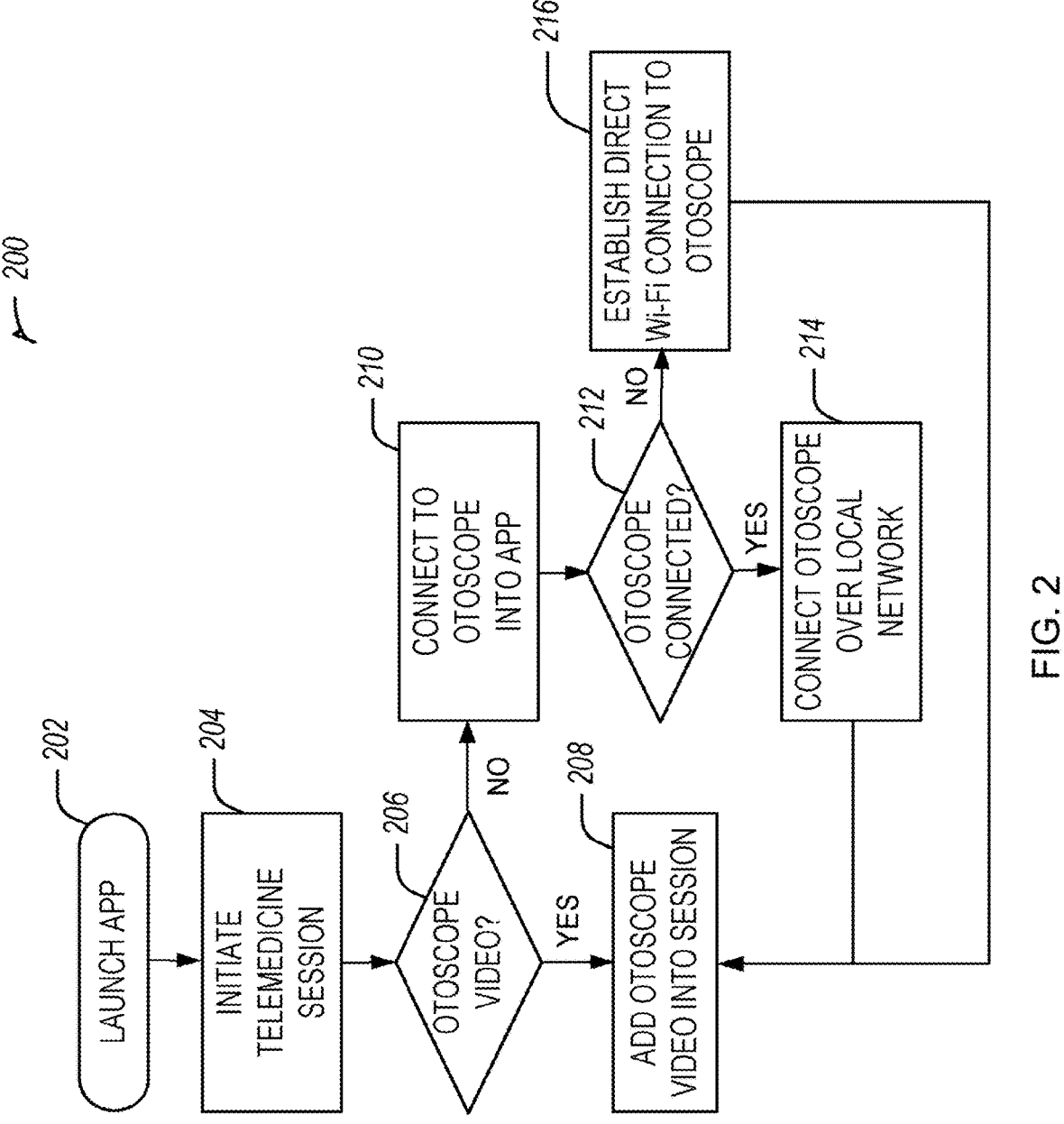
FIG. 2 illustrates a flowchart showing a technique for adding a video enabled Wi-Fi otoscope into a telemedicine session running on a mobile device in accordance with at least one example of this disclosure.

FIG. 2 illustrates a flowchart showing a technique for adding a video enabled Wi-Fi otoscope into a telemedicine session running on a mobile device in accordance with at least one example of this disclosure. In this example, a technique 200 is illustrated that describes the basic process of adding a live video stream (or still image capture capability) from a mobile Wi-Fi enabled camera equipped otoscope into a telemedicine session via a mobile device. In this example, access to the telemedicine session is provided via an App running on a mobile device, such as mobile device 106. In other examples, a similar technique can be used to added otoscope video/imaging into a telemedicine session hosted on a personal computer or similar computing device accessible by the patient or in the patient's location.

At 202, the technique 200 can begin with a user (e.g., the patient or the patient's caregiver) can launch the App providing access to a telemedicine session on a mobile device. In this example, the technique 200 can continue at 204 with the user initiating the telemedicine session through the App on the mobile device. Once the telemedicine session is operating, the physician may request that the user provide imaging of the target anatomy, such as imaging of the inner ear if the telemedicine session concerns a potential ear infection (AOM). At 206, the user via the App can attempt to access imaging from an otoscope, such as otoscope 104. If the App indicates that the otoscope imaging is available, the technique 200 continues at 208 adding the imaging from the otoscope into the telemedicine session. The imaging from the otoscope can be a live video stream or captured still images or the like.

If at 206, the App does not have access to imaging from the otoscope, the technique 200 can continue at 210 with the mobile device attempting to establish a connection to the otoscope. At 212, the technique 200 can continue with the App (or mobile device via native operating system controls) determining whether the otoscope is an available device on the local network. If the otoscope is connected to the local network, the technique 200 can continue at 214 with the App (or mobile device) establishing a connection to the otoscope over the local network. Once the otoscope is communicating with the mobile device and the App, the technique 200 can continue at 208 adding the otoscope imaging into the telemedicine session.

If at 212, the otoscope is not connected to the local network, the technique 200 can continue at 216 with the App (or mobile device) establishing a direct Wi-Fi connection to the otoscope. In this step of technique 200, the mobile device must connect to a Wi-Fi network broadcast by the otoscope and continue to maintain an IP-based connection to the Telemedicine session. Presently, only devices such as an iPhone or iPad from Apple, Inc. with a cellular data connection available can maintain the Telemedicine connection during this operation. Once the otoscope and mobile device have a direct Wi-Fi connection, the technique 200 can continue at 208 with the otoscope imaging being added into the Telemedicine session.

Figure 3:
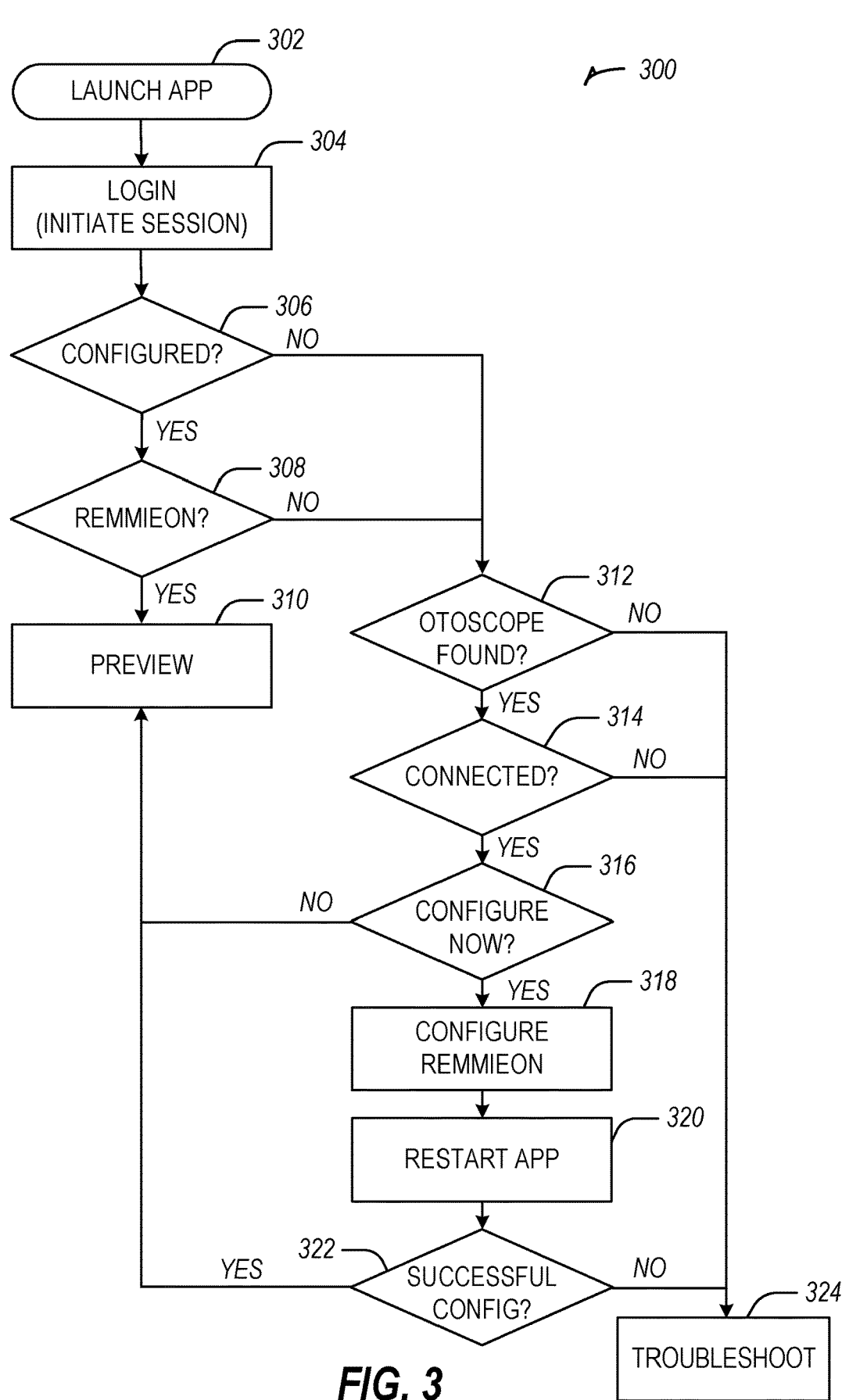
FIG. 3 illustrates a flowchart showing a technique for initiating different connection modes to a video enabled Wi-Fi otoscope in accordance with at least one example of this disclosure.

FIG. 3 illustrates a flowchart showing a technique 300 for initiating different connection modes to a video enabled Wi-Fi otoscope in accordance with at least one example of this disclosure. Technique 300 expands on the basic technique discussed in FIG. 2, with additional details regarding how the different connection modes are established and operate.

In this example, the technique 300 begins at 302 with the user launching the App on the mobile device, such as mobile device 106. At 304, the technique 300 continues with the user login to a telemedicine session to initiate a remote visit with a physician. The technique 300 can continue with imaging from an otoscope, such as otoscope 104, being requested within the Telemedicine session (via the App), which triggers the App to determine whether the otoscope is configured at 306. If the otoscope is configured, the technique 300 can continue at 308 with the App determining if the otoscope is in the RemmieOn configuration (which refers to the otoscope having an evergreen connection to the local Wi-Fi network and available for the App to communicate with over the local Wi-Fi network). If the otoscope is configured for RemmieOn, then the technique 300 can continue at 310 with providing a live Preview of the imaging from the otoscope.

If the otoscope is configured at 306, but does not have RemmieOn configured at 308, the technique 300 continues at 312 with the App determining if the otoscope is broadcasting a Wi-Fi signal. If a Wi-Fi signal is detected from the otoscope at 312, the technique 300 can continue at 314 with the App (mobile device) connecting to the otoscope Wi-Fi network. If the App can connect to the otoscope Wi-Fi network at 314, then the technique 300 continues at 316 with an option to configure the otoscope for an evergreen connection to a local Wi-Fi network (e.g., RemmieOn). However, in some use cases, such as no local Wi-Fi is available, the technique 300 continues without further configuration of the otoscope. In this case, the technique 300 continues at 310 with the App access imaging from the otoscope over the otoscope direct Wi-Fi connection to provide a Preview within the telemedicine session.

If the user selects the option to configure the otoscope at 316, the technique 300 continues at 318 with the App enabling configuration of the otoscope to make an evergreen connection with a local Wi-Fi network. At 318, the App prompts the user to select the desired local Wi-Fi network and provide a password (if it is secured). App then transmits the Wi-Fi and password information to the otoscope and prompts the otoscope to establish a connection with the selected local Wi-Fi network. At 320, the technique 300 continues with the user restarting the App. Note, aspects of technique 300 can be omitted if the user is launching the App at 302 specifically to configure the otoscope for RemmieOn (an evergreen local network connection). For example, the technique 300 can be reduced to operations 302, 306, 312, 314, 316, 318 and 320. In this example, the technique 300 concludes at 322 by determining whether the otoscope has been properly configured for local network access (e.g., RemmieOn).

Figure 4:
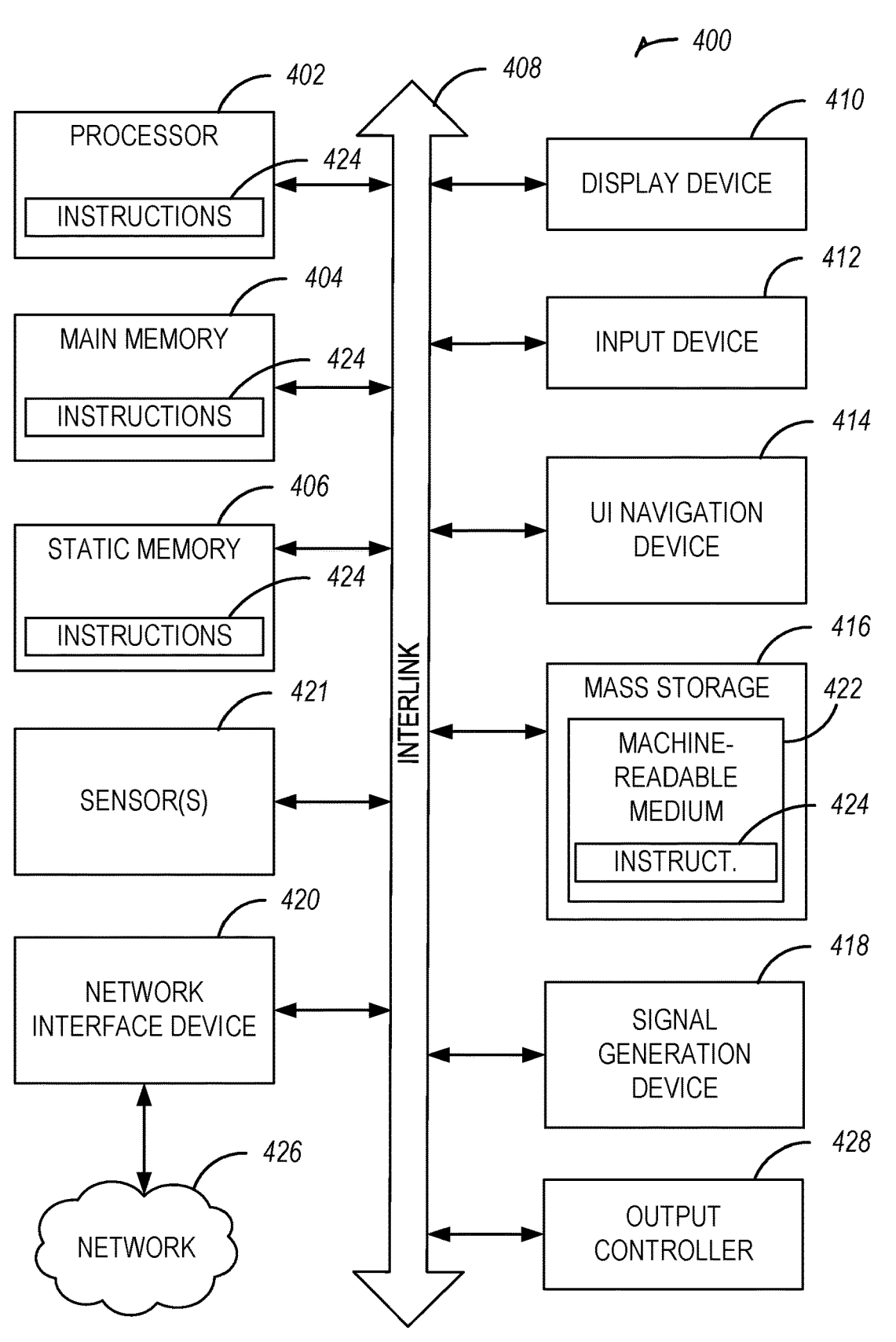
FIG. 4 illustrates a block diagram of an example machine upon which any one or more of the techniques discussed herein may perform in accordance with at least one example of this disclosure.

FIG. 4 illustrates a block diagram of an example machine 400 upon which any one or more of the techniques discussed herein may perform in accordance with some embodiments. In alternative embodiments, the machine 400 may operate as a standalone device and/or may be connected (e.g., networked) to other machines. In a networked deployment, the machine 400 may operate in the capacity of a server machine, a client machine, or both in server-client network environments. In an example, the machine 400 may act as a peer machine in peer-to-peer (P2P) (or other distributed) network environment. The machine 400 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 400 may include a hardware processor 402 (e.g., a central processing unit (CPU), a graphics processing unit (GPU), a hardware processor core, or any combination thereof), a main memory 404 and a static memory 406, some or all of which may communicate with each other via an interlink (e.g., bus) 408. The machine 400 may further include a display unit 410, an alphanumeric input device 412 (e.g., a keyboard), and a user interface (UI) navigation device 414 (e.g., a mouse). In an example, the display unit 410, input device 412 and UI navigation device 414 may be a touch screen display. The machine 400 may additionally include a storage device (e.g., drive unit) 416, a signal generation device 418 (e.g., a speaker), a network interface device 420, and one or more sensors 421, such as a global positioning system (GPS) sensor, compass, accelerometer, or other sensor. The machine 400 may include an output controller 428, such as a serial (e.g., Universal Serial Bus (USB), parallel, or other wired or wireless (e.g., infrared (IR), near field communication (NFC), etc.) connection to communicate and/or control one or more peripheral devices (e.g., a printer, card reader, etc.).

The storage device 416 may include a machine readable medium 422 on which is stored one or more sets of data structures or instructions 424 (e.g., software) embodying or utilized by any one or more of the techniques or functions described herein. The instructions 424 may also reside, completely or at least partially, within the main memory 404, within static memory 406, or within the hardware processor 402 during execution thereof by the machine 400. In an example, one or any combination of the hardware processor 402, the main memory 404, the static memory 406, or the storage device 416 may constitute machine readable media.

While the machine readable medium 422 is illustrated as a single medium, the term "machine readable medium" may include a single medium or multiple media (e.g., a centralized or distributed database, and/or associated caches and servers) configured to store the one or more instructions 424. The term "machine readable medium" may include any medium that is capable of storing, encoding, or carrying instructions for execution by the machine 400 and that cause the machine 400 to perform any one or more of the techniques of the present disclosure, or that is capable of storing, encoding or carrying data structures used by or associated with such instructions. Non-limiting machine-readable medium examples may include solid-state memories, and optical and magnetic media.

The instructions 424 may further be transmitted or received over a communications network 426 using a transmission medium via the network interface device 420 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 420 may include one or more physical jacks (e.g., Ethernet, coaxial, or phone jacks) or one or more antennas to connect to the communications network 426. In an example, the network interface device 420 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 400, and includes digital or analog communications signals or other intangible medium to facilitate communication of such software.

Each of the following non-limiting examples may stand on its own, or may be combined in various permutations or combinations with one or more of the other examples.

Example 1 is a method for merging an otoscope video stream into a telemedicine session, the method comprising: initiating, on a mobile computing device, a telemedicine session; determining, from within the telemedicine session, whether a connection to an otoscope providing a video stream is available; and accessing, if the connection is available, the video stream.

In Example 2, the subject matter of Example 1 can optionally include establishing, if the connection is not available, a connection with the otoscope.

In Example 3, the subject matter of Example 2 can optionally include establishing the connection with the otoscope includes determining whether the otoscope is connected to a local network.

In Example 4, the subject matter of Example 3 can optionally include establishing, if the otoscope is connected to the local network, a connection to the otoscope from the mobile computing device over the local network during the telemedicine session.

In Example 5, the subject matter of Example 3 can optionally include establishing, if the otoscope is not connected to the local network, a direct connection to the otoscope from the mobile computing device over a network generated by the otoscope during the telemedicine session.

In Example 6, the subject matter of Example 5 can optionally include accessing the video stream, within the telemedicine session, includes accessing the video stream over the direct connection to the otoscope.

In Example 7, the subject matter of Example 5 can optionally include accessing the video stream over the direct connection includes accessing the video stream over a Wi-Fi network generated by the otoscope.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:
1. A method for merging a video stream into a telemedicine session, the method comprising:

initiating, on a mobile computing device, a telemedicine session;

determining, from within the telemedicine session, whether a local network for providing the video stream between an otoscope and the mobile computing device is available, wherein the otoscope is configured to generate a direct connection for providing the video stream;

establishing, based on availability of the local network, a connection between the mobile computing device and the otoscope via the local network or the direct connection generated by the otoscope; and sharing, from the mobile computing device, the video stream generated by the otoscope.

2. The method of claim 1, wherein establishing the connection between the mobile computing device and the otoscope comprises determining whether the otoscope is connected to the local network.

3. The method of claim 2, wherein, in response to determining that the otoscope is connected to the local network, establishing the connection between the otoscope and the mobile computing device via the local network during the telemedicine session.

4. The method of claim 2, wherein, in response to determining that the otoscope is not connected to the local network, establishing the connection between the otoscope and the mobile computing device via the direct connection generated by the otoscope during the telemedicine session.

5. The method of claim 4, wherein accessing the video stream, within the telemedicine session, includes comprises accessing the video stream via the direct connection to the otoscope.

6. The method of claim 5, wherein accessing the video stream via the direct connection comprises accessing the video stream via a Wi-Fi network generated by the otoscope.

7. The method of claim 1, further comprising:

receiving, by a remote device, the video stream, wherein the video stream comprises a live video stream.

8. The method of claim 1, wherein the direct connection comprises a wired connection between the otoscope and the mobile computing device.

9. A system for generating an otoscope video stream within a telemedicine session, the system comprising:

processing circuitry; and memory including instructions, which when executed, cause the processing circuitry to:

initiate a telemedicine session;

determine, from within the telemedicine session, whether a local network for providing the otoscope video stream between an otoscope and a device is available, wherein the otoscope is configured to generate a direct connection for providing the otoscope video stream;

establish, based on availability of the local network, a connection between the device and the otoscope via the local network or the direct connection generated by the otoscope; and share, from the device, the otoscope video stream generated by the otoscope.

10. The system of claim 9, wherein the processing circuitry establishes the connection between the otoscope and the device comprises determining whether the otoscope is connected to the local network.

11. The system of claim 10, wherein, in response to determining that the otoscope is connected to the local network, the processing circuitry establishes the connection between the otoscope and the device via the local network during the telemedicine session.

12. The system of claim 10, wherein, in response to determining that the otoscope is not connected to the local network, the processing circuitry establishes the connection between the otoscope and the device via the direct connection generated by the otoscope during the telemedicine session.

13. The system of claim 12, wherein the processing circuitry accesses the otoscope video stream, within the telemedicine session, via the direct connection.

14. The system of claim 13, wherein the processing circuitry accesses the otoscope video stream via a Wi-Fi network generated by the otoscope.

15. At least one machine-readable medium including instructions for generating providing otoscope video stream within a telemedicine session, which when executed by processing circuitry, cause the processing circuitry to perform operations to:

initiate a telemedicine session;

determine, from within the telemedicine session, whether a local network for providing the otoscope video stream between an otoscope and a device is available, wherein the otoscope is configured to generate a direct connection for providing the otoscope video stream;

establish, based on availability of the local network, a connection between the device and the otoscope via the local network or the direct connection generated by the otoscope; and share, from the device, the otoscope video stream generated by the otoscope.

16. The at least one machine-readable medium of claim 15, wherein the processing circuitry establishes the connection between the device and the otoscope comprises determining whether the otoscope is connected to the local network.

17. The at least one machine-readable medium of claim 16, wherein, in response to determining that the otoscope is connected to the local network, the processing circuitry establishes the connection between the otoscope and the device via the local network during the telemedicine session.

18. The at least one machine-readable medium of claim 16, wherein, in response to determining that the otoscope is not connected to the local network, the processing circuitry establishes the connection between the otoscope and the device via the direct connection generated by the otoscope during the telemedicine session.

19. The at least one machine-readable medium of claim 18, wherein the processing circuitry accesses the otoscope video stream, within the telemedicine session, via the direct connection to the otoscope.

* * * * *